United States Patent [19]

Puri

[11] Patent Number: 5,204,449

[45] Date of Patent: Apr. 20, 1993

[54] ANTIGEN ANTIBODY CONJUGATE FOR MAJOR HISTOCOMPATIBILITY COMPLEX (MHC) CLASS I OR II ANTIGENS

[75] Inventor: Nirdosh K. Puri, Bayswater, Australia

[73] Assignee: Bunge (Australia) Pty. Ltd., Melbourne, Australia

[21] Appl. No.: 296,229

[22] Filed: Jan. 11, 1989

[30] Foreign Application Priority Data

Jan. 12, 1988 [AU] Australia .................... PI6256
Mar. 28, 1988 [AU] Australia .................... PI7470

[51] Int. Cl.⁵ .................... C07K 7/00; C07K 15/28
[52] U.S. Cl. .................... 530/391.7; 530/300; 530/311; 530/313; 530/387.3; 530/398; 530/399; 530/403; 530/806; 530/388.7; 530/388.73; 530/388.75; 530/388.2; 436/819
[58] Field of Search ............ 530/389, 391, 398, 399, 530/403, 806, 808, 387.3, 388.7, 388.73, 388.75, 391.1, 300, 311, 313; 436/543, 547, 548, 819

[56] References Cited

U.S. PATENT DOCUMENTS 4,950,480  8/1990  Barber et al. .................... 424/85.8

FOREIGN PATENT DOCUMENTS 8705398  9/1987  PCT Int'l Appl. .

OTHER PUBLICATIONS

G. Carayanniotis et al, *Nature*, 327, 59–61, 1987.
A. Lanzavecchia et al, *Nature*, 334, 530–532, 1988.
C. A. Sunderland et al, *Journal Immunology*, 127, 2614–2615, 1981.
Bittle et al, *Nature* vol. 298, Jul. 1982, pp. 30–33.
Clarke et al, *Nature* vol. 330, Nov. 1987, pp. 381–384.
Milstein and Cuello, *Nature* vol. 305, Oct. 1983, pp. 537–540.
Milstein and Cuello, *Immunology Today*, vol. 5, 1984, pp. 299–304.
Galfre et al, *Nature* vol. 266, 1977, pp. 550–552.
Gogolin-Ewins et al, *Immunology* 56, 1985, pp. 717–723.
Puri et al, *Veterinary Immunolgy and Immunopathology* 15, 1987, pp. 59–86.
Francis et al, *Nature* vol. 300 (1987), pp. 168–170.

*Primary Examiner*—David Saunders
*Attorney, Agent, or Firm*—Merchant & Gould

[57] ABSTRACT

An antigen antibody conjugate is provided including at least one antigen and at least one monoclonal antibody having a specificity for at least one major histocompatibility complex (MHC) class I or class II antigens and at least one monoclonal antibody having a specificity for at least one antigen other than a MHC class I or class II antigen. Each antibody is conjugated to at least one antigen.

3 Claims, No Drawings

ANTIGEN ANTIBODY CONJUGATE FOR MAJOR HISTOCOMPATIBILITY COMPLEX (MHC) CLASS I OR II ANTIGENS

The present invention relates to antibody-antigen conjugates and in particular to monoclonal antibody-antigen conjugates, a method for the preparation thereof and use thereof.

A number of agents have been utilised in the prior art as carrier molecules with limited success in delivery systems for therapeutic agents. Carrier molecules such as DNA, liposomes, proteins such as Tetanus toxoid protein, steroid hormones and antibodies have been used in conjunction with a broad spectrum of pharmaceutical or cytotoxic agents and antibiotics. Such systems have been used alone or in the presence of various adjuvants such as Freund's complete adjuvant. The limited success of such systems has in general been related to lack of target specificity and decreased efficacy in vivo. Moreover, many carrier molecules or adjuvants are expensive and in some cases have been banned by regulatory authorities. Emulsions using Freund s complete adjuvant have been reported to cause carcass damage through. abscess or granuloma formation, lead to the persistence of mineral oil residues in the carcass and/or render the animal T.B. positive. Obviously these problems severely limit or preclude the acceptance of animals for slaughter and human consumption. Moreover, the immune response generated may not be of significant magnitude and the quality thereof may be delayed and may be variable, particularly in outbred animal species.

It has been suggested in the prior art to utilise antibodies as carrier molecules for the targeting of a compound or compounds for delivery to specific cells. However, whilst this system has provided some improvement, the lack of specificity still remains a problem and the prior art has concentrated on delivery of cytotoxic agents and pharmaceuticals.

Moreover, the use of monoclonal antibodies as carriers has been characterised by a system of covalent bonding to the active compound. This has presented complex and difficult Problems of alteration in antibody specificity and/or in the activity of the conjugated compound and/or subsequent cleavage and activation. For example where the target system is internalised, there is no assurance that the conjugated compound will be released in its active form.

Accordingly, it is an object of the present invention to overcome, or at least alleviate, one or more of the difficulties related to the prior art.

Accordingly, in a first aspect of the present invention there is provided an antigen-antibody conjugate including at least one antigen; and
at least one monoclonal antibody having a specificity for at least one major histocompatability complex (MHC) class I or II antigen; the at least one monoclonal antibody being conjugated to the at least one antigen.

The major histocompatability Class I antigens are glycoproteins which may be present on a variety of human and animal tissues and cells. Three primary class I gene products have been identified in man (termed HLA-A, -B, -C) and in mouse (termed H-2K, -D, -L).

The major histocompatability complex class II antigens are glycoproteins which may be present on the surface of B-cells, activated T lymphocytes or antigen presenting cells including monocytes, macrophages, and B lymphocytes. Two distinct class II antigens, I-A and I-E, have been defined in the mouse whilst at least three or four distinct class II antigens (HLA-DR, -DQ, -DP) are identifed in man.

The at least one monoclonal antibody may be modified for attachment to the at least one antigen. For example, where the antibodies are of IgG or IgM isotype, a linker may be attached to the carbohydrate end thereof. The carbohydrate end may be modified for attachment to a linker, for example by oxidation thereof.

The at least one monoclonal antibody may be a mouse monoclonal antibody. The at least one monoclonal antibody may be raised against sheep MHC class II molecules.

The at least one monoclonal antibody having a specificity for at least one MHC class II antigen may be selected from the monoclonal antibodies SBU II 28-1, 37-68, 38-27, 42-20 and 49-1. All the monoclonal antibodies described above are of the IgG1 isotype except SBU II 37-68 and 49-1 which are IgG-2a. All of the monoclonal antibodies except monoclonal antibody SBU II 49-1 recognise one of four distinct sub-sets of class II molecules in sheep. The monoclonal antibody SBU 49-1 recognises all four sub-sets of class II molecules.

The at least one monoclonal antibody having a specificity for at least one MHC class I antigen may be selected from the monoclonal antibodies SBU I41-17, 41-19, 47.3 and 41-28. These monoclonal antibodies have been described in Gogolin-Ewens et al. (1985) Immunology, 56:714–224 and in Puri et al. (1987), Vet. Immunol. Immunopathol. 15:59–86. Samples of the abovementioned monoclonal antibodies are maintained in the Culture Collection, University of Melbourne, Department of Veterinary Science, Parkville, Victoria, Australia.

The at least one antigen may be of any suitable type. The at least one antigen may be selected from proteins, Peptides including hormones, pharmaceutical or cytotoxic agents, agents which bind with DNA including alkylating agents and antibiotics, anti-metabolites such as methotrexate, agents. which act on cell surfaces and protein synthesis inhibitors.

The at least one antigen, in a preferred aspect, may be a protein or peptide which is not antigenic per se, but is antigenic in the presence of a carrier molecule.

In a particularly preferred form the antigen may be selected for its ability to provide an immunogenic effect. In this preferred form, the antigen-antibody conjugate is for use in a species other than that in which the monoclonal antibody has been raised, where the monoclonal antibody per se may function immunogenically. For example, the monoclonal antibodies described above are raised in mice so that they are antigenic in other animals such as domestic animals including sheep, as well as humans.

Accordingly, the at least one antigen may be selected from antigens which normally require a carrier molecule and/or adjuvant to exhibit immunogenicity. However no such carrier molecule and/or adjuvant may be necessary. The monoclonal antibody may replace the carrier molecule and/or adjuvant.

Furthermore, the use of the class II monoclonal antibody-antigen conjugate in mice may result in specific targeting to immune cells as described previously enabling a new approach to creating monoclonal antibodies to antigens that are otherwise poorly immunogenic.

Whilst we do not wish to be restricted by the theory, it is postulated that the class II monoclonal antibody, when conjugated to the desired compound, is most likely enhancing immunogenicity by providing (i) appropriate B and or T cell epitopes which result in the immune response to the mouse immunoglobulin augmenting the immune response to the protein or peptide conjugated thereto.

(ii) a specific targeting effect to immune effector cells that express class II molecules, i.e. monocytes, macrophages, B cells or activated T cells. This is likely to result in (a) a much lower dose of antigen than is normally required to elicit an immune response, (b) reproducible responses between members of a given species, (c) administration of soluble antigen antibody conjugates, i.e. no FCA or other adjuvant or oil emulsion required.

In a preferred form, the at least one antigen may be selected from hormones, analogues thereof and derivatives thereof. The at least one antigen may be selected from hormones including: follicle stimulating hormone (FSH) which is a hormone which may be used to regulate the reproductive functions in animals; luteinizing hormone-releasing hormone (LH-RH) and or fragments of FSH or luteinizing hormone (LH) such as the -subunits thereof, which are hormones which may be used for desexing of animals; or growth hormone regulating hormones including somatostatin, analogues thereof, fragments thereof or derivatives thereof.

The at least one antigen may be a peptide. The Peptide may be a synthetic peptide. The peptide may be derived from Foot and Mouth Disease Virus (FMDV) VP1 surface protein (Bittle et al. (1982), Nature 298: 30-33; Francis et al. 1987, Nature 300: 168-170; Clark et al 1987, Nature 300: 381-384.) Difficulties have been encountered in the prior art in generating sufficient and/or consistent immune response thereto in the prior art.

In addition, the invention relates to the subsequent use of the antibodies produced in various animal species in response to the desexing, growth promoting, FMDV or any other monoclonal antibody based vaccines. These antibodies may be of use in hormone and/or other diagnostic assays, either in the form of sera from immunized animals, as hybridoma derived monoclonal antibodies or otherwise purified and suitably derived antibodies in soluble form or coupled to standard solid matrix supports.

The at least one antigen may be modified for attachment to the monoclonal antibody in any suitable manner.

The conjugation of the at least one monoclonal antibody and the at least one antigen may be conducted in any suitable manner. For example, the coupling may be of a physical and/or chemical type. The antibody and antigen may be coupled physically utilising a carrier for example a Sepharose carrier (available from Pharmacia Chemicals Pty. Uppsalla, Sweden).

Alternatively or in addition, the antigen and antibody may be chemically linked. Any standard linking system may be used. A linking system such as the avidin-biotin system may be used to link the antigen onto the monoclonal antibody.

Accordingly, in a preferred aspect of the present invention there is provided a process for the preparation of an antibody-antigen conjugate which process includes providing at least one antigen bearing a hydrazide group, and at least one oxidised monoolonal antibody having a specificity for at least one MHC class I or class II antigen, and bearing reactive aldehyde groups mixing the at least one hydrazide-modified antigen with the at least one oxidised monoclonal antibody isolating the reaction product produced thereby.

The advantages of the preferred process of conjugation is that the monoclonal antibody is substantially unaffected by the conjugation. Little or no loss of specificity or activity is encountered.

Alternatively or in addition, the antigen in question may be chemically linked to a carrier molecule such as Protein A. Protein A is a polypeptide of bacterial origin having affinity for the Fc portion of the immunoglobulins of various species including mouse. In particular for mouse monoclonal antibodies of subclass IgG2a, 2b or 3, Protein A binds with high affinity and with minimal resultant loss of antibody activity. For example, for primary immunizations, a soluble monoclonal antibody SBU II 37-68 (page 14, paragraph 3) LH-RH hydrazide-Protein A complex could be administered. Secondary and/or subsequent immunizations would be of the form SBU II 37-68-LH-RH hydrazide-Protein A, or a chemically linked Protein A-LH-RH complex may be used.

The hydrazide-modified antigen may be formed in any suitable manner. Where the antigen is a protein or peptide and is produced synthetically, the hydrazide modification may be incorporated in the protein or peptide synthesis.

The oxidised monoclonal antibody may be formed utilising any suitable chemical or enzymatic process. An oxidation catalyst may be used. It will be understood that the oxidation at least Partially modifies the carbohydrate of the antibody to aldehyde groups thus rendering them reactive with. the hydrazide groups on the antigen.

It will be understood that utilising the antibody antigen complex according to the present invention the immune response generated for the specific targeted MHC class I or II antigens produces an adjuvant-free immune response which may be up to ten times or more greater relative to that of the immune response generated utilising non-specific (i.e. control, non MHC reactive) monoclonal antibodies.

In a further aspect of the present invention, there is provided an antigen-antibody conjugate including at least one antigen; and at least one monoclonal antibody having a specificity for at least one major histocompatability complex (MHC) class I or II antigen; and at least one monoclonal antibody having a specificity for at least one antigen other than a MHC Class I or II antigen;

each antibody being conjugated to the at least one antigen.

One or more antigens may be simultaneously targeted to one or more lymphocyte or monocyte/macrophage antigens (see Table 2 below). For example the at least one antigen(s) may be conjugated to two monoclonal antibodies, one to CD4 like molecules including CD4+cells and one to MHC class II molecules, thus targeting T-helper (CD4+) cells in addition to monocytes, macrophages and/or B-lymphocytes bearing the MHC Class II Molecules. This may provide an enhanced humoral immune response.

Alternatively, the at least one antigen may be conjugated to two monoclonal antibodies, one to CD8 like molecules including CD8+cells and one to MHC Class I molecules, thus targeting the CD$^8$+cells and/or the immune effect or cells bearing MHC Class I molecules. In this embodiment, such targeting may result in enhanced cellular immune response.

Similarly the antigen-antibody conjugate according to this aspect of the present invention may be formed by the physical or chemical linking of two different monoclonal antibodies one of which has specificity for the antigen of interest and the other being used to target the conjugate (i.e. Antibody-Antibody-antigen) to the desired lymphocyte antigen or MHC Class I or II surface molecule.

In a further alternative aspect of the present invention, the at least one monoclonal antibody may be formed from a hetero-hybridoma or "quadroma".

Quadromas are described in Nature 305:537–540, 1983; Immunol. Today 5 (10): 299–304. 1984). Quadromas are capable of secreting a single bi-specific (i.e. with dual specificity for desired antigen and lymphocyte target) monoclonal antibody. For example a monoclonal antibody with specificity for MHC class I or II antigens and hormones such as LH-RH may be produced. This monoclonal antibody may be reacted with LH-RH and the resulting complex used for immunization.

Both of the above embodiments share the advantage that they overcome the necessity to chemically link antigen and antibody.

It will be understood that the hormones such as luteinising hormone releasing hormone (LH-RH) and/or subunits of follicle stimulating hormone (FSH) and/or luteinizing hormone (LH) or fragments thereof and/or growth hormones including growth hormone regulating hormones such as somatostatin by themselves are poorly antigenic because of their small size and, in order to obtain antibodies against them, it has been necessary in the prior art to attach hormones to much larger natural or synthetic carrier molecules. Numerous techniques for attachment of hormones to various carrier molecules are known but these techniques are not easy to control and it is very difficult to obtain conjugates of a predictable and of consistent quality. It will be understood that with the antigen-antibody conjugate according to the present invention the MHC class I or II specific monoclonal antibodies, being themselves immunogenic, may preferably make it unnecessary to include an additional carrier molecule with hormones such as LH-RH, LH, FSH and somatastatin. Moreover specific targeting to the immune effector cells renders adjuvants unnecessary and allows the administration of soluble antigen to the animal.

Accordingly, in a preferred aspect of the present invention, the antigen-antibody conjugate may include at least one antigen, which is a hormone selected from a luteinizing hormone releasing hormone (LH-RH), follicle stimulating hormone (FSH), luteinizing hormone (LH) and somatostatin, analogues thereof, fragment thereof or derivative thereof; and at least one monoclonal antibody having a specificity for major histocompatability complex (MHC) class I or II antigens and at least one monoclonal antibody having a specificity for the CD4 or CD8 like molecules of a given species.

The major histocompatability complex class I or II antibodies may also be conjugated with agents selected from proteins, peptides including hormones, pharmaceutical or cytotoxic agents, agents which bind with DNA including alkylating agents, antibiotics, antimetabolites such as methotrexate, agents which act on cell surfaces and protein synthesis inhibitors.

The pharmaceutical or veterinary composition according to the present invention may be utilised with any human or animal species Animal species including cattle, sheep, goats, cats, guinea pigs, pigs, dogs, reindeer, horses, chickens, ducks, turkeys and primates may be so treated.

According to a further aspect of the present invention, there is provided a method of inhibiting the reproductive functions of animals which method includes
 providing
  an antigen-antibody conjugate including
   at least one antigen; and
   at least one monoclonal antibody having a specificity for at least one major histocompatability complex (MHC) class I or II antigen; the at least one monoclonal antibody being conjugated to the at least one antigen; and
  administering an effective amount of the antigen-antibody conjugate to an animal to be treated.

The method of inhibiting the reproductive functions of animals may include preventing or suppressing ovulation and/or oestrus in female animals and prevention or suppression of sperm production and/or sexual behaviour in male animals.

The contaceptive conjugate may be provided in the form of a vaccine. The vaccine may be administered parentarily. Parental administration may include subcutaneous, intramuscular or intravenous injection, oral administration or absorption through the skin or by mini-pump either implanted in the animal or attached to the hide thereof.

The dose rates effective will vary with the weight and species of animals. Optimum dose rates for individual species may be selected utilising simple experimentation.

However, as a guide for animals such as pigs and sheep each dose may include from approximately 5 to 30 microgram of suitably conjugated LH-RH or -FSH or LH or a fragment thereof.

The dosage regimen may include a primary vaccination followed by one or more secondary vaccinations. If desired, the primary vaccination may be made with the hormone-antibody conjugate. Secondary and subsequent vaccinations may be made utilising standard hormone formulations.

In addition, multimers of a particular peptide antigen may be used. For example the LH-RH peptide or an appropriate peptide fragment of FSH or LH may be caused to polymerize into a synthetic protein by the addition of cysteine residues at the N-and C-termini. This may be achieved by using appropriate amino acids as spacers. Multimers of LH-RH and or of particular portions of the subunits of LH and/or FSH may also be constructed at the DNA level using recombinant techniques to manipulate the gene (DNA) encoding an indigenous peptide hormone or a particular epitope thereof, in order to obtain repeating coding sequences for a multimer of this sequence.

According to a further aspect of the present invention there is provided a pharmaceutical or veterinary growth promoting conjugate of somatostatin and at least one monoclonal antibody having a specificity for major histocompatability complex class I or class II antigens; and at least one monoclonal antibody having a specificity for CD4 or CD8 like molecules of a given species;

each monclonal antibody being conjugated to the somatostatin.

The somatostatin-monoclonal antibody growth promoting conjugate may be administered to promote growth and improve food conversion efficiency in humans and animals including cattle, sheep, pigs and chickens. The somatostatin-monoclonal antibody conjugate may be administered either alone or in admixture with various diluents, carriers or excipients chosen with respect to the intended method of administration.

The dose rates effective will carry with the weight and species of animals. Optimum dose rates for individual species may be selected utilising simple experimentation.

However, as a guide for animals such as pigs and sheep each dose may include from approximately 5 to 30 microgram of suitably conjugated somatostatin.

The growth promoting conjugate may for a growth promoting vaccine include a primary vaccination followed by one or more secondary vaccinations. If desired, the primary vaccination may be made with the hormone-antibody conjugate. Secondary and subsequent vaccinations may be made utilising standard hormone formulations.

The somatostatin-monoclonal antibody conjugate may be administered to promote growth and improve food conversion efficiency in humans and animals as discussed above. The conjugate may also be administered for the treatment of protein accumulation deficiencies and protein loss in mammals.

The present invention will now be more fully described with reference to the accompanying examples. It should be understood, however, that the description following is illustrative only and should not be taken in any way as a restriction on the generality of the invention described above.

EXAMPLE 1

Monoclonal Antibody Production

A variety of immunogens were used for antibody production. For monoclonal antibody SBU II 28-1, alveolar macrophages were collected by lung lavage using phosphate-buffered saline (PBS). Cells were washed three times in PBS and between $5\times10^6$ and $10^7$ cells were injected intraperitoneally at weekly intervals for 4 weeks. For monoclonal antibodies SBU.II 38-27 and 49-1, efferent duct lymphocytes from a cannulated prescapular lymph node were used as the immunogen. The immunization schedule was essentially as for SBU-.II 28-1. Monoclonal antibody SBU.II 37-68 was raised by allo-immunization between A.TH and A.TL mice. Splenocytes ($10^7$) from A.TL mice were injected intraperitoneally into A.TH mice at weekly intervals for 6 weeks and sera tested for reactivity with sheep lymphocytes. Mice with high titres against sheep lymphocytes were subsequently boosted and used. for fusion. For the monoclonal antibody SBU.II 42-20, mice rceived purified lymphocyte glycoproteins (50 ug in Freund's complete adjuvant) injected intraperitoneally and in serveral subcutaneous sites. This was repeated weekly for 4 weeks. Mice were then boosted 3-4 weeks later with 100 ug of antigen in complete Freund's adjuvant. Three or four days prior to fusion, a final intravenous injection of $5\times10^6$ cells or 50 ug of glycoprotein in PBS was administered. Fusion of splenic lymphocytes with P3-NS/1-Ag4-1 (NS-1) cells was carried out according to Galfre et al. (1977), Nature, 255: 550-552. All other procedures involving cell cultures were as described in Gogolin-Ewens et al. (1985), Immunology, 35: 717-724.

Hybrid supernatants were screened for activity against fresh sheep lymphocytes according to the assay described by Williams, Galfre & Milstein (1977), Cell 12: 663-673. The isotypes of the monoclonal antibodies were determined using a three step radioimmunoassay procedure with rabbit anti-mouse IgG subclass specific antisera (Chemicon International, Los Angeles, California) as second antibody and [125I]horse anti-rabbit F(ab')2 (HAR) as the third antibody Rabbit anti-mouse F(ab')2 (RAM) and HAR were the kind gift of A.F. Williams, Oxford.

The seven hybridomas selected on this basis were designated as SBU.II 28-1, 38-27, 38-64, 38-30, 42-20, 37-68 and 49-1. All the monoclonal antibodies are of the IgG1 isotype except SBU.II 37-68 and 49-1 are which is IgG-2a. The monoclonal antibodies all appear to recognize non-polymorphic determinants on sheep lymphocytes.

Using sequential immunoprecipitation four distinct subsets of class II molecules were identified by the monoclonal antibodies SBU.II 28-1, 37-68, 38-27 and 42-20, while another monoclonal antibody, SBU.II 49-1, recognized all four subsets of class II molecules.

EXAMPLE 2

Immune Response to MonoClonal Antibodies

For the measurement of primary immune responses sheep were injected intravenously on days 1, 3 and 5 with 100 ug of DE-52 purified monoclonal antibody in 0.9% of NaCl or with 1 mg of control mouse monoclonal IgG (mIgG). For the measurement of secondary immune responses sheep were reinjected with the same. dose of the appropriate antigen on days 14, 16 and 18 as described above.

Serum antibody titres were determined by ELISA. For each antigen the range of titres represents the results from three sheep.

The results of the immunisation with the monoclonal antibodies as antigens is shown in Table 1.

These results illustrate the effect of targeting, in particular enhanced immune response to a soluble administered anti-Class II antibody over that of control mouse IgG in a 10-fold greater amount.

TABLE 1

| Antigen used for | Serum Antibody Titre | | | |
|---|---|---|---|---|
| Immunization | Day 7 | Day 14 | Day 21 | Day 28 |
| SBU.II 38-27 | 1/10 | 1/200–1/2000 | 1/5000–1/10,000 | 1/5000–1/10,000 |
| SBU.II 37-68 | 1/10 | 1/20–1/200 | 1/5000–1/10,000 | 1/5000–1/10,000 |
| SBU.II 49-1 | 1/10 | 1/20–1/200 | 1/1000 | 1/2000–1/5000 |

TABLE 1-continued

| Antigen used for Immunization | Serum Antibody Titre | | | |
|---|---|---|---|---|
| | Day 7 | Day 14 | Day 21 | Day 28 |
| SBU.II 28-1 | 1/2–1/5 | 1/20–1/50 | 1/200 | 1/1000–1/2000 |
| SBU.II 42-20 | 1/2–1/5 | 1/20–1/50 | 1/200 | 1/200 |
| mIgG | 1/2–1/5 | 1/20–1/200 | 1/500–1/1000 | 1/1000 | a Control mouse monoclonal IgG of isotypes IgG1, 2a and 2b.

EXAMPLE 3

Immune Response to Monoclonal Antibodies

Additional monoclonal antibodies which exhibit antigen specificity and which may be used in conjunction with the monoclonal antibody-antigen complex as described above are set out in Table 2.

TABLE 2

Examples of additional sheep lymphocyte antigens defined by monoclonal antibodies and suitable for targeting with foreign antigens.

| Monoclonal antibody (clone number) | Antigen Specificity and published reference | Human analogue of antigen |
|---|---|---|
| 44-38, 44-97 | SBU-T4 (Immunology 55: 739-749, 1985) | CD4 (T4) |
| 38-65 | SBU-T8 (Immunology 55: 739-749, 1985) | CD8 (T8) |
| 41-17, 41-28 | | |
| 41-19, 47-3 | SBU-MHC CL.I (Immunology 56: 717-24. 1985) amd Vet. Immunol. Immunopathol. 1987, 15:59-86. | MHC Class I |

EXAMPLE 4

Immune Response to Antigen-Antibody Conjugate

A test conjugate was created utilising conjugates of anti-class II MHC Monoc Antibodies 38-27 and 37-68 conjugated to a test antigen, the egg white protein Avidin. Avidin is a suitable test antigen due to its biotin-binding capabilities Monoclonal antibody 38-27 was biotinylated using the standard N=hydroxysuccinimide (NHSS) ester of biotin.

Monoclonal antibody 37-68 was biotinylated using biotin hydroxide.

For primary immunizations, sheep were injected intradermally thrice over seven days with either 1.0 mg Avidin or 1.0 mg of a monoclonal antibody-avidin-conjugate.

Secondary immunizations commenced at day 70, following the same protocol as for primary immunizations.

Antibody titres are reported in Table 3. A very significant enhancement in the immune response to the antigen-antibody conjugate is clearly evident Preparation and testing of a variety of monoclonal antibody-antigen conjugates including conjugates of the abovementioned monoclonal anbitobides 38-27 and 37-68 with Somatostatin have also now been completed. Similar results showing high titre anti-somatostatin immune response in sheep may be achieved.

TABLE 3

| Sheep No. | Immunogen | Primary Anti-Avidin Titre a | | Secondary Anti-Avidin Titre b |
|---|---|---|---|---|
| | | Day 7 | Day 70 | |
| 16 | Avidin | 1/500 | 1/500 | 1/1000 |
| 17 | | | | |
| 18 | | | | |
| 19 | 38-27: NHSS- | 1/5000 | 1/5000 | 1/20000 |
| 20 | Biotin-Avidin | –1/10000 | –1/10000 | |
| 22 | 37-68: NH-NH2 Biotin-Avidin | 1/10000 | 1/10000 | 1/50000 |

TABLE 3

Antibody titres were determined by ELIZA. For
a. primary immunizations sheep were injected thrice (intradermally) over seven days with either 1.0 mg Avidin or 1.0 mg of a monoclonal antibody-avidin-conjugate (Monoclonal antibody:Avidin molar ratio of 1: 0.5).
b. Secondary immunizations commenced at day 70, following the same protocol as for primary immunizations.
c. Monoclonal antibody 38-27 was biotinylated using the standard N-hydroxysuccinamide (NHSS) ester of biotin.
d. Monoclonal antibody 37-68 was biotinylated using biotin hydrazide.

Finally, it is to be understood that various other modifications and/or alterations may be made without departing from the spirit of the present invention as outlined herein.

I claim:

1. An antigen-antibody conjugate including:
   (a) at least one antigen selected from the group consisting of luteinizing hormone releasing hormone, follicle stimulating hormone, luteinizing hormone and somatostatin, analogues thereof, fragments thereof, mixtures thereof;
   (b) at least one monoclonal antibody having a specificity for major histocompatibility complex (MHC) class I or class II antigens;
   (c) at least one monoclonal antibody having a specificity for the CD4 or CD8 molecules of a given species; and,
   (d) each antibody being conjugated to the at last one antigen.

2. An antigen-antibody conjugate including
   at least one antigen; and at least one monoclonal antibody having a specificity for at least one major histocompatibility complex (MHC) class II antigen; and
at least one monoclonal antibody having a specificity for CD4+ cells;
each antibody being conjugated to the at least one antigen.

3. An antigen antibody conjugate including at least one antigen; and
at least one monoclonal antibody having a specificity for at least one major histocompatibility complex (MHC) class I antigen; and
at least one monoclonal antibody having a specificity for CD8 molecules;
each antibody being conjugated to the at least one antigen.

* * * * *

UNITED STATES PATENT AND TRADEMARK OFFICE
CERTIFICATE OF CORRECTION

PATENT NO. : 5,204,449　　　　　　　　　　Page 1 of 2
DATED　　　 : April 20, 1993
INVENTOR(S) : Nirdosh K. Puri It is certified that error appears in the above-indentified patent and that said Letters Patent is hereby corrected as shown below:

Column 4, line 5, after the word "includes", insert --:--.

Column 4, lines 7 and 11, delete "oxidised" and insert therefor --oxidized--.

Column 4, line 36, delete "oxidised" and insert therefor --oxidized--.

Column 4, line 39, delete "Partially" and insert therefor --partially--.

Column 4, line 41, after the word "with", delete ".".

Column 5, lines 36 and 37, delete "luteinising" and insert therefor --luteinizing--.

Column 6, line 18, after the word "includes", insert --:--.

Column 6, lines 33 and 34, delete "behaviour" and insert therefor --behavior--.

Column 6, line 35, delete "contaceptive" and insert therefor --contraceptive--.

Column 8, line 3, after the word "used", delete ".".

Column 8, line 11, delete "106" and insert therefor --$10^6$--.

Column 8 line 25, delete "125I" and insert therefor --$125_I$--.

Column 8, line 32, after the numeral "49-1", delete "are".

Column 8, line 49, after the word "same", delete ".".

Column 8, line 55, delete "immunisation" and insert therefore --immunization--.

Column 9, line 33, delete "Monoc" and insert therefore --Monoclonal--.

UNITED STATES PATENT AND TRADEMARK OFFICE
CERTIFICATE OF CORRECTION

PATENT NO. : 5,204,449
DATED : April 20, 1993
INVENTOR(S) : Nirdosh K. Puri

It is certified that error appears in the above-indentified patent and that said Letters Patent is hereby corrected as shown below:

Column 9, line 55, delete "antibides" and insert therefore --antibodies--.

Column 10, line 16, after the word "Biotin" insert --Avidin--.

Column 10, line 34, before the word "Antibody" insert --a. --.

Column 10, line 65, in claim 1, delete "last" and insert therefore --least--.

Signed and Sealed this

Twenty-sixth Day of September, 1995

Attest:

BRUCE LEHMAN

Attesting Officer

Commissioner of Patents and Trademarks